US00PP37548P2

(12) United States Plant Patent
Li

(10) Patent No.: US PP37,548 P2
(45) Date of Patent: Jul. 28, 2026

(54) ***PORTULACA* PLANT NAMED 'NUFPO24051'**

(50) Latin Name: *Portulaca oleracea*
Varietal Denomination: NUFPO24051

(71) Applicant: KLEMM + SOHN GMBH & CO. KG, Stuttgart (DE)

(72) Inventor: Ruijun Li, North Parramatta (AU)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/242,565

(22) Filed: Jun. 18, 2025

(51) Int. Cl.
*A01H 5/02* (2018.01)
*A01H 6/00* (2018.01)

(52) U.S. Cl.
USPC ..... Plt./471

(58) Field of Classification Search
USPC ..... Plt./471
CPC ..... A01H 5/02; A01H 5/00; A01H 6/00
See application file for complete search history.

(56) References Cited

PUBLICATIONS

Ball Seed PortoGrande Red Portulaca, retrieved on Sep. 30, 2025 at https://info.ballseed.com/PlantInfo/?phid=052305975004463, one page. (Year: 2025).*
Danziger Mega Pazzaz Red, retrieved on Sep. 30, 2025 at https://www.danzigeronline.com/catalog/annuals/mega-pazzaz-red/, 6 pp. (Year: 2025).*
Google translation from Russian to English, retrieved on Sep. 30, 2025 2 pages. (Year: 2025).*
Radsadspb 2025, retrieved on Sep. 30, 2025 at https://radsadspb.ru/f/opt_predlozhenie_no4_ukorenennye_cherenki_odnoletnih_rastenij.pdf, 16 pp. (Year: 2025).*

* cited by examiner

*Primary Examiner* — June Hwu
(74) *Attorney, Agent, or Firm* — Weatherly IP Solutions, LLC; John E. Pritchard; James M. Weatherly

(57) ABSTRACT

A new *Portulaca* plant designated 'NUFPO24051' particularly distinguished by small, red, early maturing flowers; and compact and spreading plant habit.

1 Drawing Sheet

Genus and species: *Portulaca oleracea.*
Variety denomination: 'NUFPO24051'.

BACKGROUND OF THE NEW PLANT

The present invention comprises a new and distinct variety of *Portulaca*, botanically known as *Portulaca oleracea*. and hereinafter referred to by the variety name 'NUFPO24051'. 'NUFPO24051' originated from a controlled cross in December 2017 at Cobbitty, Australia between the proprietary female *Portulaca* variety PO17.2.01 (unpatented) and the proprietary male *Portulaca* parent PO17.2.09 (unpatented).

Seeds from the controlled cross were obtained. The seeds were sown and plants were grown for evaluation. A single plant was selected in November 2018 and subsequently named 'NUFPO24051'. In December 2018 'NUFPO24051' was first vegetatively propagated by vegetative stem cuttings in Cobbitty, Australia. 'NUFPO24051' was found to reproduce true to type in successive generations of asexual propagation via stem cuttings in Cobbitty, Australia.

SUMMARY

The following are the most outstanding and distinguishing characteristics of 'NUFPO24051' when grown under normal horticultural practices in Cobbitty, Australia:

1. Small, red, early maturing flowers; and
2. Compact and spreading plant habit.

DESCRIPTION OF THE PHOTOGRAPH

This new *Portulaca* plant is illustrated by the accompanying photograph of a 16-week-old plant grown outdoors in Stuttgart, Germany during August 2024. The colors shown are as true as can be reasonably obtained by conventional photographic procedures. The photograph is a whole plant photo of 'NUFPO24051' and shows the foliage, buds, and flowers.

DESCRIPTION

The following detailed descriptions set forth the distinctive characteristics of 'NUFPO24051'. The data which define these characteristics were collected from asexual reproductions carried out in Cobbitty, Australia from 3-month-old plants in 2019. Color references are to The R.H.S. Colour Chart of The Royal Horticultural Society of London (R.H.S.), 5$^{th}$ edition (2007).

Classification:
*Family.*—Portulacaceae.
*Botanical.*—*Portulaca oleracea.*
*Designation.*—'NUFPO24051'.
*Type.*—Purslane.

Parentage:
*Female parent.*—'PO17.2.01' (*P. oleraceae*, unpatented).
*Male parent.*—PO17.2.09 (*P. oleraceae*, unpatented).

Plant description:
*Habit and form.*—Compact and spreading.

*Height.*—3.8 cm.
*Spread.*—23 cm.
*Time and conditions to produce a rooted cutting.*—5 to 8 days.
*Life cycle.*—Annual.
*Flowering requirements.*—Spring to Autumn.

Stems:
*General description.*—Round with slight ridges.
*Stem color.*—145A.
*Anthocyanin.*—Absent.
*Pubescence.*—Absent.
*Diameter.*—0.28 cm.
*Length.*—13.0 cm to 20.0 cm.
*Internode length.*—1.8 cm.
*Branching.*—Abundant.

Leaves:
*Arrangement.*—Alternate, simple.
*Shape.*—Obovate.
*Apex.*—Acute.
*Base.*—Rounded.
*Margin.*—Entire.
*Leaf attachment.*—Petiolate.
*Leaf length.*—1.9 cm.
*Leaf width.*—1.2 cm.
*Leaf thickness.*—0.15 cm.
*Texture.*—Upper surface: Smooth, glabrous, succulent. Lower surface: Smooth, glabrous, succulent.
*Leaf color.*—Immature upper surface: 138B (green) with very narrow reddish margin 53A. Immature lower surface: 138B. Mature upper surface: 137B (green) with narrow weak reddish margin 53A. Mature lower surface: 138B.
*Leaf surface pubescence.*—Absent.
*Venation.*—Pinnate.
*Petiole.*—Length: 0.2 cm. Diameter: 0.15 cm. Color: 145B.
*Fragrance.*—None detected.

Inflorescence:
*Type.*—Solitary, sessile.
*Flowering habit.*—Freely flowering habit and most flowers face upright.
*Time to bloom from propagation.*—Approximately 8 weeks.
*Lastingness of individual blooms on the plant.*—1 to 2 days.
*Flower diameter.*—3.4 cm to 3.6 cm.
*Flower depth.*—1.1 cm.
*Fragrance.*—None detected.

Flower bud:
*Surface appearance and texture.*—Shiny, pubescent.
*Shape.*—Ovoid.
*Bud length.*—0.9 cm.
*Bud diameter.*—0.6 cm.
*Bud color.*—144A.

Corolla:
*Shape of petals.*—Obovate.
*Petal pubescence.*—Smooth, glabrous.
*Petal size.*—Length: 1.8 cm. Width: 1.2 cm.
*Petal apex.*—Emarginate.
*Petal margin.*—Entire.
*Petal color.*—Upper surface: 43B with a base (center) close to 13B (yellow). Lower surface: 41D.
*Average number of petals per flower.*—5.
*Intensity of overlapping petals.*—Weak.
*Depth of the emarginated petal apex.*—Shallow.

Calyx:
*Arrangement.*—Two and base fused.
*Sepals.*—Shape: Deltoid. Apex: Acute. Margin: Entire. Length: 0.8 cm. Diameter: 0.6 cm. Color: 146D. Texture: Upper surface: Smooth. Lower surface: Smooth. Appearance: Double lobed.

Reproductive organs:
*Stamens.*—Number per flower: 50 to 57. Form: Free. Color: Anther: 17A. Filament: 145D. Length: 0.6 cm. Pollen amount: Abundant. Pollen color: 23A.
*Fragrance.*—Absent.
*Placental arrangement.*—Central. Pistil number per flower: 1. Pistil length: 1.3 cm. Stigma color: 145D. Stigma length: 0.3 cm. Style length: 1.1 cm. Style color: 145D.

Seeds:
*Production.*—About 10 seeds per flower.
*Diameter.*—1.0 mm.
*Color.*—200B.

Disease and insect resistance: No disease or insect resistance observed.

COMPARISON WITH PARENTAL AND COMMERCIAL VARIETIES

'NUFPO24051' is distinguished from the parents as described in Table 1.

TABLE 1

Comparison with Parental Varieties

| Characteristic | 'NUFPO24051' | Female parent PO17.2.01 | Male parent PO17.2.08 |
|---|---|---|---|
| Flower color | Red | Magenta | Red |
| Flower size | Larger than 17.2.01 | Smaller than NUFPO24051 | Similar to NUFPO24051 |
| Earliness | Earlier than PO17.2.08 | Similar to NUFPO24051 | Later than NUFPO24051 |

'NUFPO24051' can be compared to the commercial *Portulaca* variety 'Mega Pazzaz Red' (unpatented). Differences between the varieties are described in Table 2.

TABLE 2

Comparison with Similar Commercial Variety

| Characteristic | 'NUFPO24051' | 'Mega Pazzaz Red' |
|---|---|---|
| Flower size | Smaller than 'Mega Pazzaz Red' | Larger than 'NUFPO24051' |
| Earliness | Earlier than 'Mega Pazzaz Red' | Later than 'NUFPO24051' |

I claim:

1. A new and distinct variety of *Portulaca* plant designated 'NUFPO24051' as illustrated and described herein.

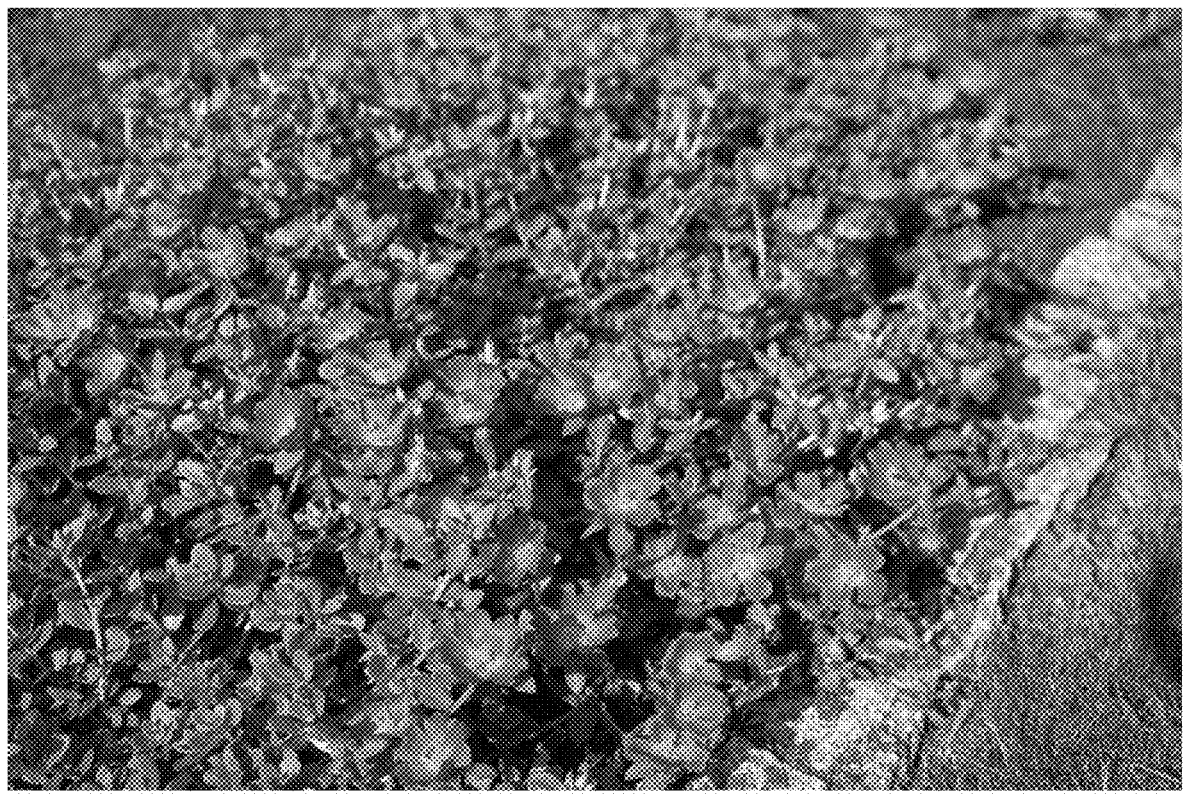

* * * * *